United States Patent
Hendriks

(10) Patent No.: US 7,245,374 B2
(45) Date of Patent: Jul. 17, 2007

(54) OPTICAL ANALYSIS SYSTEM

(75) Inventor: Robert Frans Maria Hendriks, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/539,193

(22) PCT Filed: Nov. 21, 2003

(86) PCT No.: PCT/IB03/05467

§ 371 (c)(1), (2), (4) Date: Dec. 19, 2005

(87) PCT Pub. No.: WO2004/057284

PCT Pub. Date: Jul. 8, 2004

(65) Prior Publication Data

US 2006/0176471 A1 Aug. 10, 2006

(30) Foreign Application Priority Data

Dec. 19, 2002 (EP) .................................. 02080427

(51) Int. Cl.
*H01J 40/14* (2006.01)
(52) U.S. Cl. .................................................. 356/326
(58) Field of Classification Search ...................... None
See application file for complete search history.

(56) References Cited

U.S. PATENT DOCUMENTS

| 5,090,807 | A | 2/1992 | Tai |
| 5,737,076 | A | 4/1998 | Glaus et al. |
| 6,198,531 | B1 | 3/2001 | Myrick et al. |
| 6,430,513 | B1* | 8/2002 | Wang et al. ................... 702/28 |
| 6,870,629 | B1* | 3/2005 | Vogel et al. ................. 356/519 |
| 2006/0158734 | A1* | 7/2006 | Schuurmans et al. ....... 359/485 |

* cited by examiner

*Primary Examiner*—Tu T. Nguyen

(57) ABSTRACT

An optical analysis system (1), which is arranged to determine amplitude of a principal component of an optical signal, includes a first detector (5) for detecting the optical signal weighted by a first spectral weighting function, and a second detector (6) for detecting the optical signal weighted by a second spectral weighting function. For an improved signal-to-noise ratio, the optical analysis system (1) further includes a dispersive element (2) for spectrally dispersing the optical signal, and a distribution element (4) for receiving the spectrally dispersed optical signal and for distributing a first part of the optical signal weighted by the first spectral weighting function to the first detector (5) and a second part of the optical signal weighted by the second spectral weighting function to the second detector (6). The optical analysis system (1) is suited for use in numerous applications including a spectroscopic analysis system (30) and a blood analysis system (40).

10 Claims, 5 Drawing Sheets

OPTICAL ANALYSIS SYSTEM

CROSS REFERENCE TO RELATED APPLICATIONS

This application is a 35 USC § 371 National Stage application of PCT Application PCT/I03/05467 filed Nov. 21, 2003, which claims the benefit under 35 USC § 119(a) of European Patent Office (EPO) Application No. 02080427.4 filed Dec. 19, 2002.

BACKGROUND

The invention relates to an optical analysis system for determining an amplitude of a principal component of an optical signal, the optical analysis system comprising a first detector for detecting the optical signal weighted by a first spectral weighting function, and a second detector for detecting the optical signal weighted by a second spectral weighting function.

The invention also relates to a spectroscopic analysis system comprising such an optical analysis system.

The invention also relates to a blood analysis system comprising such an optical analysis system.

U.S. Pat. No. -B1-6,198,531 discloses an embodiment of an optical analysis system described in the opening paragraph.

The known optical analysis system is part of a spectroscopic analysis system suited for, e.g., analyzing which compounds are comprised at which concentrations in a sample. It is well known that light interacting with the sample carries away information about the compounds and their concentrations. The underlying physical processes are exploited in optical spectroscopic techniques in which light of a light source such as, e.g., a laser, a lamp or light-emitting diode is directed to the sample for generating an optical signal which carries this information.

For example, light may be absorbed by the sample. Alternatively or in addition, light of a known wavelength may interact with the sample and thereby generate light at a different wavelength due to, e.g., a Raman process. The transmitted and/or generated light then constitutes the optical signal which may also be referred to as the spectrum. The relative intensity of the optical signal as function of the wavelength is then indicative of the compounds comprised in the sample and their concentrations.

The optical signal has to be analyzed so as to identify the compounds comprised in the sample and to determine their concentrations. In the known optical analysis system the optical signal is analyzed by dedicated hardware comprising an optical filter. This optical filter has a transmission which depends on the wavelength, i.e. it is designed to weigh the optical signal by a spectral weighting function which is given by the wavelength dependent transmission. The spectral weighting function is chosen such that the total intensity of the weighted optical signal, i.e. of the light transmitted by the filter, is directly proportional to the concentration of a particular compound. This intensity can then be conveniently detected by a detector such as, e.g., a photo-diode. For every compound a dedicated optical filter with a characteristic spectral weighting function is used. The optical filter may be, e.g., an interference filter having a transmission constituting the desired weighting function.

For successful implementation of this analysis scheme it is essential to know the spectral weighting functions. They may be obtained, e.g., by performing a principal component analysis of a set comprising N spectra of N pure compounds of known concentration where N is an integer. Each spectrum comprises the intensity of the corresponding optical signal at M different wavelengths, where M is an integer as well. Typically, M is much larger than N. Each spectrum containing M intensities at corresponding M wavelengths constitutes an M-dimensional vector whose M components are these intensities. These vectors are subjected to a linear-algebraic process known as singular value decomposition (SVD) which is the core of principal component analysis and is well understood in this art.

As a result of the SVD a set of N eigenvectors $z_n$, with n being a positive integer smaller than N+1, is obtained. The eigenvectors $z_n$ are linear combinations of the original N spectra and often referred to as principal components or principal component vectors. Typically, the principal components are mutually orthogonal and determined as normalized vectors with $|z_n|=1$. Using the principal components $z_n$, the optical signal of a sample comprising the compounds of unknown concentration may be described by the combination of the normalized principal components multiplied by the appropriate scalar multipliers:

$$x_1z_1+x_2z_2+\ldots+x_nz_n,$$

The scalar multipliers $X_n$, with n being a positive integer smaller than N+1, may be considered as the amplitudes of the principal components $z_n$ in a given optical signal. Each multiplier $x_n$ can be determined by treating the optical signal as a vector in the M dimensional wavelength space and calculating the direct product of this vector with a principal component vector $z_n$. This yields the amplitude $x_n$ of the optical signal in the direction of the normalized eigenvector $z_n$. The amplitudes $x_n$ correspond to the concentrations of the N compounds.

In the known optical analysis system the calculation of the direct product of the vector representing the optical signal and the eigenvector representing the principal component is implemented in the hardware of the optical analysis system by means of the optical filter. The optical filter has a transmittance such that it weighs the optical signal according to the components of the eigenvector representing the principal component, i.e. the principal component vector constitutes the spectral weighting function. The filtered optical signal can be detected by a detector which generates a signal with an amplitude proportional to the amplitude of the principal component and hence to the concentration of the corresponding compound.

In a physical sense, each principal component is a constructed "spectrum" with a shape in a wavelength range within the optical signal. In contrast to a real spectrum, a principal component may comprise a positive part in a first spectral range and a negative part in a second spectral range. In this case the vector representing this principal component has positive components for the wavelengths corresponding to the first spectral range and negative components for the wavelengths corresponding to the second spectral range.

An embodiment of the known optical analysis system is designed to perform the calculation of the direct product of the vector representing the optical signal and the eigenvector representing the principal component in the hardware in cases where the principal component comprises a positive part and a negative part. To this end, a part of the optical signal is directed to a first filter which weighs the optical signal by a first spectral weighting function corresponding to the positive part of the principal component, and a further part of the optical signal is directed to a second filter which weighs the optical signal by a second spectral weighting function corresponding to the negative part of the principal component. The light transmitted by the first filter and by the second filter is detected by a first detector and a second detector, respectively. The signal of the second detector is then subtracted from the signal of the first detector, resulting in a signal with an amplitude corresponding to the concentration.

In another embodiment the known optical analysis system is able to determine the concentrations of a first compound and of a second compound by measuring the amplitudes of a corresponding first principal component and of a second principal component. To this end, a part of the optical signal is directed to a first filter which weighs the optical signal by a first spectral weighting function corresponding to the first principal component, and a further part of the optical signal is directed to a second filter which weighs the optical signal by a second spectral weighting function corresponding to the second principal component. The light transmitted by the first filter and by the second filter is detected by a first detector and a second detector, respectively. The signals of the first detector and the second detector correspond to the amplitudes of the first principal component and of the second principal component, respectively.

It is a disadvantage of the known optical analysis system that the signal-to-noise ratio is relatively low.

SUMMARY

It is an object of the invention to provide an optical analysis system of the kind described in the opening paragraph, which is capable of providing a signal with a relatively high signal-to-noise ratio.

The invention is defined by the independent claims. The dependent claims define advantageous embodiments.

According to the invention the object is realized in that the optical analysis system further comprises a dispersive element for spectrally dispersing the optical signal, and a distribution element for receiving the spectrally dispersed optical signal and for distributing a first part of the optical signal, weighted by the first spectral weighting function, to the first detector and a second part of the optical signal, weighted by the second spectral weighting function, to the second detector.

The invention is based on the insight that the signal to noise ratio is relatively low in the known optical analysis system, because a significant part of the optical signal is not detected by any of the detectors, but blocked by, e.g., the first optical filter or the second optical filter. For instance, the optical signal received by the first optical filter comprises all information but the first filter transmits only the part of the optical signal corresponding to the first weighting function whereas the part of the optical signal corresponding to the second weighting function is blocked by the filter. The light blocked by the first optical filter and the second optical filter is not detected, leading to a reduced signal-to-noise ratio.

According to the invention this reduction of the signal-to-noise ratio is at least partly avoided. To this end, the optical analysis system comprises a dispersive element such as, e.g., a grating or a prism for spectrally dispersing the optical signal. The spectrally dispersed optical signal is received by a distribution element, i.e. different parts of the distribution element receive different wavelengths of the optical signal. For individual wavelengths the distribution element is arranged to distribute a first part of the optical signal, weighted according to the first spectral weighting function, to the first detector and a second part of the optical signal, weighted according to the second spectral weighting function, to the second detector. Thus, instead of partly blocking the optical signal as is done by the first optical filter and the second optical filter of the known optical analysis system, the different parts of the optical signal are directed to different detectors. As a consequence a larger amount of the optical signal is detected, yielding an improved signal-to-noise ratio.

According to the invention the optical signal is not restricted to optical signals having wavelengths which are visible to the human eye. The optical signal may comprise spectral components in the ultraviolet (UV) and/or in the infrared (IR) spectral range. Here, the IR spectral range may comprise the near infrared (NIR) and the far infrared (FIR) which has a frequency above 1 THz, and all intermediate wavelengths as well.

According to the invention the principal component is not limited to a pure principal component. Here, a pure principal component refers to a mathematically exact eigenvector for a certain compound. A principal component may also comprise minor contributions from other compounds which may result from imperfections in the determination of the principal components. A principal component may also correspond to a mixture of several compounds of known concentration.

In an embodiment the principal component comprises a positive part in a first spectral range and a negative part in a second spectral range, the first part of the optical signal weighted by the first spectral weighting function corresponding to the positive part, the second part of the optical signal weighted by the second spectral weighting function corresponding to the negative part, the first detector and the second detector being coupled to a signal processor arranged to subtract a signal generated by the second detector from a signal generated by the first detector. In this embodiment an optical signal comprising a principal component having a positive part and a negative part can be analyzed with an improved signal-to-noise ratio. Typically, the first spectral range is free from the second spectral range.

In another embodiment the principal component comprises a first principal component and a second principal component, the first part of the optical signal weighted by the first spectral weighting function corresponding to the first principal component, the second part of the optical signal weighted by the second spectral weighting function corresponding to the second principal component. This optical analysis system is particularly suited for analyzing samples comprising two or more compounds each having a corresponding principal component. It provides the concentrations of the two or more compounds with an improved signal-to-noise ratio.

In yet another embodiment the principal component comprises a first principal component and a second principal component, and the first principal component and/or the second principal component comprises a positive part in a first spectral range and a negative part in a second spectral range.

It is advantageous if the distribution element has a surface for receiving the spectrally dispersed optical signal, the surface comprising a first set of surface elements and a second set of surface elements, the surface elements of the first set being arranged to distribute the spectrally dispersed optical signal to the first detector, the surface elements of the second set being arranged to distribute the spectrally dispersed optical signal to the second detector. In this embodiment, each surface element receives, in dependence on its position and its surface area, a certain portion of the spectrally dispersed optical signal. The first weighting function is then determined by the positions and the surface areas of the surface elements of the first set, and the second weighting function is determined by the positions and the surface areas of the surface elements of the second set. The spectrally dispersed optical signal received by the surface may be reflected and/or diffracted by the surface. Alternatively, it may be transmitted and refracted and/or diffracted.

This embodiment has the advantage that the distribution element can be manufactured relatively easily by, e.g., using a transparent substrate such as a glass substrate which is provided with surface elements by etching and/or polishing. Alternatively, the substrate may be manufactured using an appropriately shaped mold. An additional advantage of a transparent substrate is that the optical signal loss is relatively low.

In another embodiment the distribution element comprises an array of liquid crystal cells arranged to form a first set of sub-arrays having refractive index gradients, and a second set of sub-arrays having refractive index gradients, the sub-arrays of the first set being arranged to distribute the spectrally dispersed optical signal to the first detector, the sub-arrays of the second set being arranged to distribute the spectrally dispersed optical signal to the second detector.

The index of refraction of the cell is controlled by applying a voltage to a cell of the liquid crystal array. A sub-array of cells with a refractive index gradient is created by applying different voltages to neighboring cells. The gradient can be adjusted by adjusting the voltages. The spectrally dispersed optical signal is refracted by the refractive index gradients of the sub-arrays. The sub-arrays of the first set refract the optical signal to the first detector, and the sub-arrays of the second set refract the optical signal to the second detector. In this embodiment, analogously to the embodiment described above, each sub-array receives, in dependence on its position, a certain spectral portion of the spectrally dispersed optical signal. The first weighting function is then determined by the positions and the surface areas of the sub-arrays of the first set, and the second weighting function is determined by the positions and the surface areas of the sub-arrays of the second set.

This embodiment has the advantage that the first spectral weighting function and the second spectral weighting function can be adjusted relatively easily by adjusting the voltages applied to the cells of the liquid crystal array. This is particularly useful because the same distribution element can be used to analyze optical signals comprising different principal components.

It is advantageous if the dispersive element is arranged to disperse the optical signal in a dispersive plane and the optical analysis system further comprises a focusing member for focusing the dispersed optical signal, the focusing member having a first focal distance in the dispersive plane and a second focal distance in a plane perpendicular to the dispersive plane, the first focal distance being different from the second focal distance. In this embodiment the spectrally dispersed optical signal is focused on the distribution element such that the different spectral components of the optical signal are received by different portions of the distribution element. It is then possible to selectively distribute different wavelengths to different detectors. It is advantageous if the focusing member is arranged to focus the dispersed optical signal in the dispersive plane on the distribution element.

In this embodiment it is also advantageous if the optical analysis system further comprises a further focusing member for focusing the first part of the optical signal on the first detector. This allows the use of a first detector having a relatively small detection area for efficiently detecting the first part.

For an efficient detection using detectors with an even smaller detection area it is advantageous if the optical analysis system further comprises a further dispersive element for spectrally recombining the first part of the optical signal prior to focusing the first part on the first detector. The first part of the optical signal distributed by the distribution element is in principle still spectrally dispersed, thus limiting the possibility to focus the first part to a small detection area. By using a further dispersive element, the first part of the optical signal is spectrally recombined which allows for focusing it to a smaller area. Therefore, a smaller first detector placed in this focus can be used. Alternatively, a pinhole or aperture may be placed in this focus to implement a confocal detection scheme.

BRIEF DESCRIPTION OF THE DRAWINGS

These and other aspects of the optical analysis system, the spectroscopic analysis system and the blood analysis system according to the invention will be further elucidated and described with reference to the drawings, in which.

The Figures are not drawn to scale. In general, identical components are denoted by the same reference numerals.

DETAILED DESCRIPTION

Figure 1A:
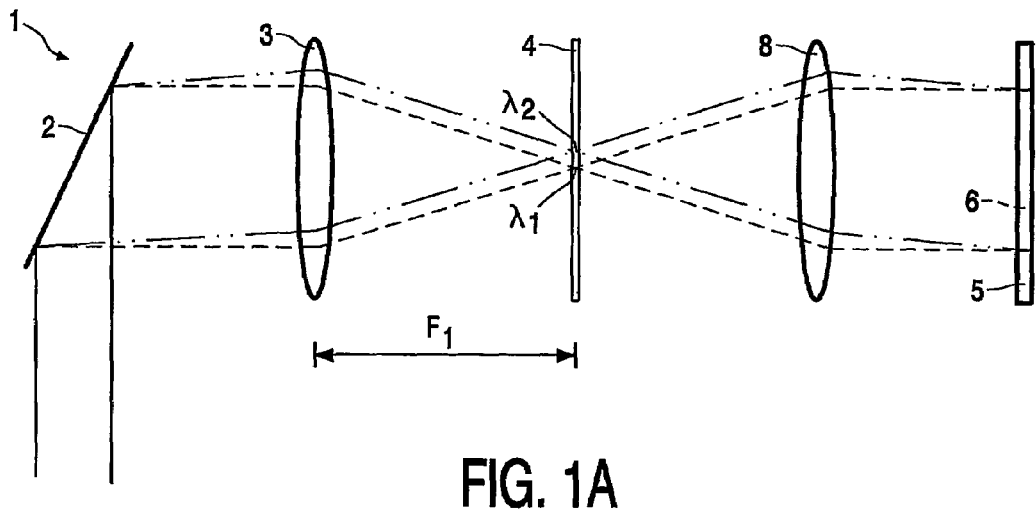
FIGS. 1A and 1B are schematic diagrams of the beam paths in the dispersive plane and in a plane perpendicular to the dispersive plane, respectively, of an embodiment of the optical analysis system.
Figure 1B:
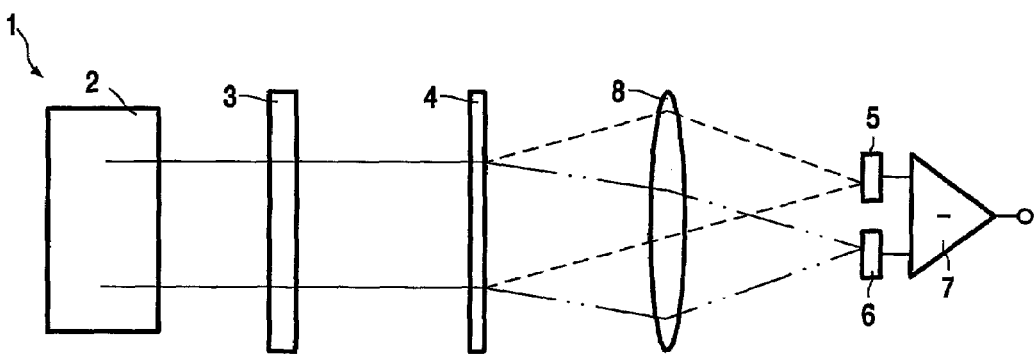

The optical analysis system 1 for determining an amplitude of a principal component of an optical signal, shown in FIGS. 1A and 1B, comprises a dispersive element 2 for spectrally dispersing the optical signal. The dispersive element 2 is a grating which spectrally disperses the optical signal in a dispersive plane. The beam paths in this dispersive plane are shown in FIG. 1A, the beam paths in a plane perpendicular to the dispersive plane being shown in FIG. 1B. Instead of a grating, other dispersive elements such as, e.g., a prism may be used.

The optical analysis system further comprises a focusing member 3 for focusing the dispersed optical signal. The focusing member 3 has a first focal distance in the dispersive plane shown in FIG. 1A and a second focal distance in a plane perpendicular to the dispersive plane shown in FIG. 1B. In this embodiment the focusing member 3 is cylinder lens which focuses the dispersed optical signal in the dispersive plane, but not in the plane perpendicular to the dispersive plane. The first focal distance $F_1$ is different from the second focal distance $F_2$ which is infinite. In alternative embodiments the focusing member 3 is an aspherical lens having two finite focal distances $F_1$ and $F_2$. Alternatively, the focusing member may be an aspherical mirror.

The focusing member 3 is arranged to focus the dispersed optical signal in the dispersive plane on the distribution element 4. In the dispersive plane, rays of different wavelengths are focused on different parts of the distribution element 4. In FIGS. 1A and 1B two rays of different wavelength are depicted by way of example by a dashed line and by a dashed double dotted line, respectively.

Figure 3:
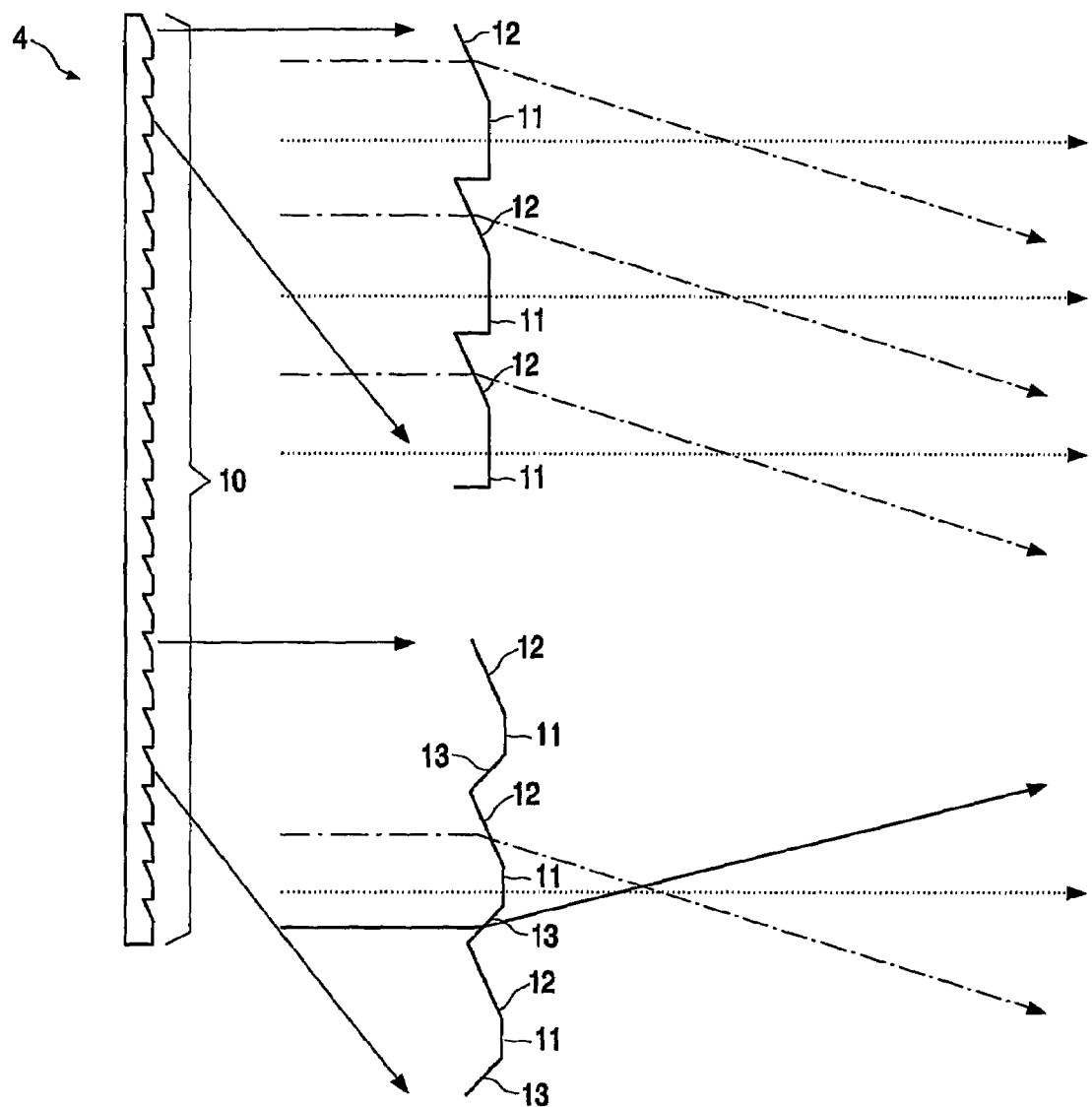
FIG. 3 is a cross-section of an embodiment of the distribution element.
Figure 4:
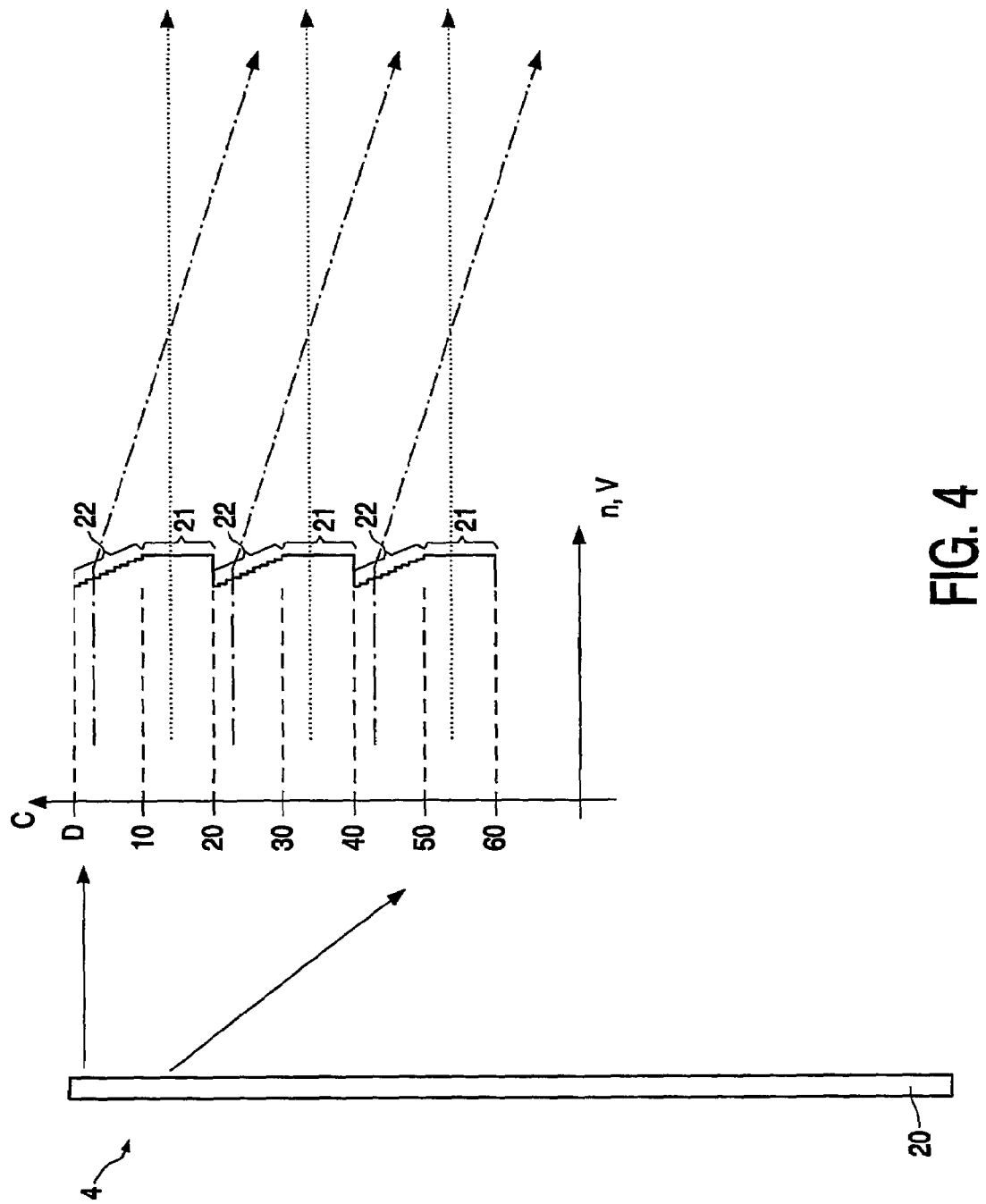
FIG. 4 is a cross-section of another embodiment of the distribution element.

The distribution element 4 receives the spectrally dispersed optical signal and distributes a first part of the optical signal, weighted by the first spectral weighting function, to a first detector 5 and a second part of the optical signal, weighted by the second spectral weighting function, to a second detector 6. Embodiments of the distribution element 4 are shown in FIGS. 3 and 4 and will be discussed below. The first detector 5 and the second detector 6 may be any type of detector suited to detect light. They may be, e.g., two separate photodiodes or a split detector.

In the embodiment shown in FIGS. 1A and 1B the optical signal comprises a principal component having a positive part in a first spectral range and a negative part in a second spectral range. A particular ray of a wavelength $\lambda_1$ of the first spectral range and a particular ray of a wavelength $\lambda_2$ of the second spectral range are depicted by the dashed line and the dashed double dotted line, respectively. The first part of the optical signal weighted by the first spectral weighting function corresponds to the positive part and is detected by the first detector 5. The second part of the optical signal weighted by the second spectral weighting function corresponds to the negative part and is detected by the second detector 6. The first detector 5 and the second detector 6 are coupled to a signal processor 7 arranged to subtract a signal generated by the second detector 6 from a signal generated by the first detector 5.

Figure 2:
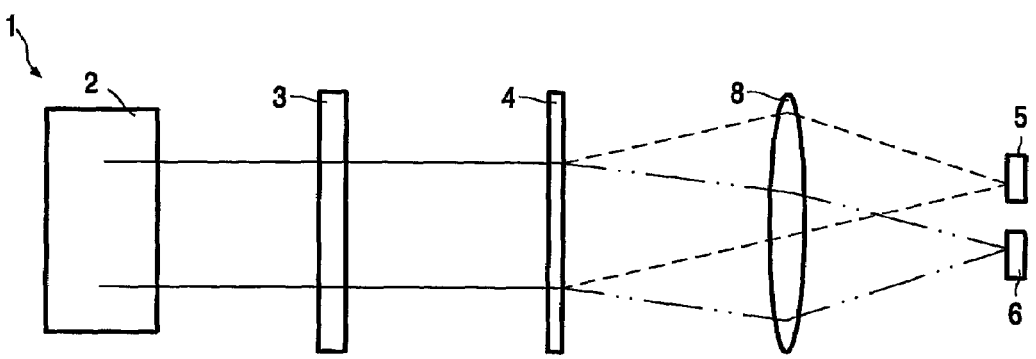
FIG. 2 is a schematic diagram of the beam paths in a plane perpendicular to the dispersive plane of another embodiment of the optical analysis system.

In another embodiment the principal component comprises a first principal component and a second principal component, the first part of the optical signal weighted by the first spectral weighting function corresponding to the first principal component while the second part of the optical signal weighted by the second spectral weighting function corresponds to the second principal component. When the first spectral weighting function and the second spectral weighting function do not overlap, the optical analysis system shown in FIGS. 1A and 1B may be used. However, when the first spectral weighting function and the second spectral weighting function overlap at least partly, it is required that the optical signal of a particular wavelength is partly detected by the first detector 5 and partly by the second detector 6. The beam paths in the dispersive plane may in this embodiment be identical to that shown in FIG. 1A. The beam paths in the plane perpendicular to the dispersive plane are shown in FIG. 2. The wavelength depicted by the dashed line is partly detected by the first detector 5 and by the second detector 6. The same holds for the wavelength depicted by the dashed double dotted line. For all wavelengths the relative amounts detected by the two detectors 5 and 6 are determined by the two spectral weighting functions. As will be explained below the distribution element 4 is designed to distribute the optical signal to the two detectors 5 and 6 accordingly.

In the embodiment shown in FIG. 3, the distribution element 4 is a transparent glass substrate which has a surface 10 for receiving the spectrally dispersed optical signal. The surface 10 comprises a first set of surface elements 11 and a second set of surface elements 12. The surface elements 11 of the first set are arranged to distribute the spectrally dispersed optical signal to the first detector 5, corresponding rays being depicted by a dotted line. The surface elements 12 of the second set are arranged to distribute the spectrally dispersed optical signal to the second detector 6, corresponding rays being depicted by a dashed dotted line. In the embodiment of FIG. 3 the surface elements 11 of the first set are mutually substantially parallel and tilted with respect to the surface elements 12 of the second set, which are mutually substantially parallel as well. This is advantageous in cases where the distribution element 4 is situated substantially in the focal plane of the focusing member 3. However, it is not essential according to the invention. In an alternative embodiment, not shown, the distribution element comprises a substrate with a concave and/or convex surface in which the surface elements are integrated. In this embodiment the distribution element may be integrated with the focusing member 3 or with the further focusing member 8.

In FIG. 3 the distribution element 4 is shown in a cross-sectional view in a plane parallel to the dispersive plane. The part of the distribution element 4 which is shown enlarged in the upper right part of FIG. 3 receives a first wavelength range of the optical signal. Because the surface elements 11 of the first set and the surface elements 12 of the second set have the same surface areas in a projection perpendicular to the propagation direction of the spectrally dispersed optical signal, 50% of the optical signal in the first wavelength range is distributed to the first detector 5 and 50% to the second detector 6, respectively.

The part of distribution element 4 which is shown enlarged in the lower right part of FIG. 3 receives a second wavelength range of the optical signal. Because of the surface areas of the surface elements 11 and of the surface elements 12 seen in a projection perpendicular to the propagation direction of the spectrally dispersed optical signal, 50% of the optical signal in the second wavelength range is distributed to the first detector 5 and 25% to the second detector 6, respectively. The surface 10 of the distribution element 4 further comprises a third set of surface elements 13 which may direct 25% of the optical signal with the wavelength of the second spectral component to a third detector or to a beam dump where it is absorbed. In this embodiment the surface elements 13 are mutually parallel, but alternatively they may have any other orientation as long as they do not distribute the optical signal to the first detector 5 or the second detector 6. The surface elements 13 may be useful in some cases to satisfy the normalization condition of the principal component vector. In this embodiment the first spectral weighting function and the second spectral weighting function are determined by the positions and the surface areas of the surface elements 11 and the surface elements 12.

In another embodiment, not shown, the distribution element 4 is similar to that shown in FIG. 3, but the spectrally dispersed optical signal is not refracted as in FIG. 3, but reflected.

The glass substrate shown in FIG. 3 is an optical element which refracts the spectrally dispersed optical signal because its optical thickness d, i.e. the index of refraction n multiplied by the geometrical thickness t, $d = t\, n$, is a function of the position. Substantially the same pattern of the optical thickness d can be obtained in an alternative embodiment as shown in FIG. 4. Instead of a glass substrate the distribution element 4 comprises an array 20 of liquid crystal elements arranged to create substantially the same pattern of the index of refraction n. To this end, a first set of sub-arrays 21 having mutually parallel refractive index gradients and a second set of sub-arrays 22 having mutually parallel refractive index gradients are formed. The refractive index gradients of the first set are tilted with respect to the refractive index gradients of the second set. Analogous to the distribution element with the surface 10 with surface elements 11 and 12, it is not essential that the refractive index gradients are mutually parallel. The index of refraction n of each column C is controlled by the voltage V applied to the cells of the column as is shown in the upper right corner of FIG. 4. The sub-arrays 21 of the first set are arranged to distribute the spectrally dispersed optical signal to the first detector 5, corresponding rays being depicted by a dotted line. The sub-arrays 22 of the second set are arranged to distribute the spectrally dispersed optical signal to the second detector 6, corresponding rays being depicted by a dashed dotted line. In this embodiment the position and the surface area of the sub-arrays 21 and 22 of the first set and the second set, respectively, determine the first spectral weighting function and the second spectral weighting function.

In the embodiment shown in FIGS. 1A, 1B and 2, the optical analysis system 1 further comprises a further focusing member 8 for focusing the first part of the optical signal on the first detector 5. In the embodiment of FIGS. 1A, 1B and 2 the further focusing member 8 is a lens. Alternatively or in addition, a focusing mirror may be used.

Figure 5A:
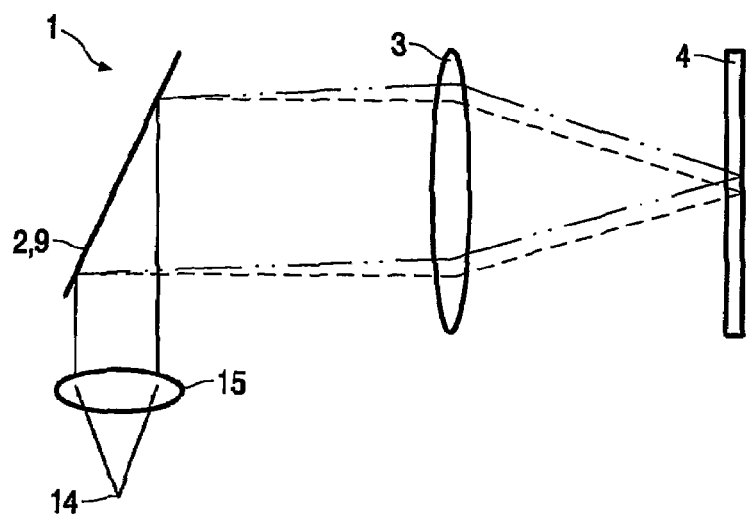
FIGS. 5A and 5B are schematic diagrams of the beam paths in the dispersive plane and in a plane perpendicular to the dispersive plane, respectively, of another embodiment of the optical analysis system, the beam paths in the plane perpendicular to the dispersive plane being unfolded for simplicity.
Figure 5B:
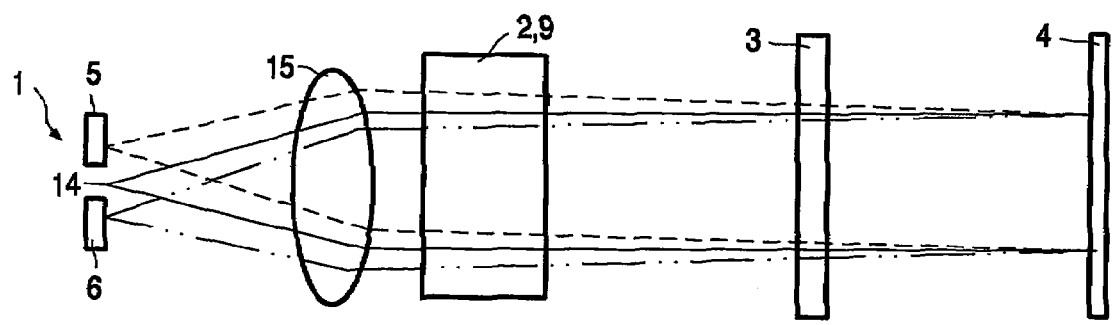

In the embodiment shown in FIGS. 5A and 5B, the optical analysis system 1 further comprises a further dispersive element 9 for spectrally recombining the first part of the optical signal prior to focusing the first part on the first detector 5. In this embodiment the optical signal enters the optical analysis system 1 from a point source 14 which may be, e.g., a pinhole in a confocal detection scheme. The optical analysis system 1 comprises a lens 15 for collimating the optical signal, and a dispersive element 2, being a grating, and a focusing member 3, being a cylinder lens, analogously to the optical analysis system 1 shown in the FIGS. 1A, 1B and 2. The focusing member 3 is arranged to focus the dispersed optical signal on the distribution element 4. In this embodiment the distribution element 4 shown in FIG. 3 is arranged to reflect the dispersed optical signal back towards the focusing member 3 for re-collimation. The re-collimated optical signal is then still spectrally dispersed; this limits the possibility to focus it to a relatively small spot size. To spatially recombine the optical signal it is sent to the fixer dispersive element 9 which in this embodiment is the dispersive element 3, i.e. the dispersive element 3 and the further dispersive element 9 are integrated in one grating. The spectrally recombined optical signal weighted by the first spectral weighting function and the spectrally recombined optical signal weighted by the second spectral weighting function are focused on the first detector 5 and the second detector 6 by the lens 15.

In another embodiment, not shown, the distribution element 4 transmits and refracts the spectrally dispersed optical signal and the further dispersive element 9 is arranged to spectrally recombine the optical signal weighted by the first spectral weighting function prior to focusing it on the first detector 5.

Figure 6:
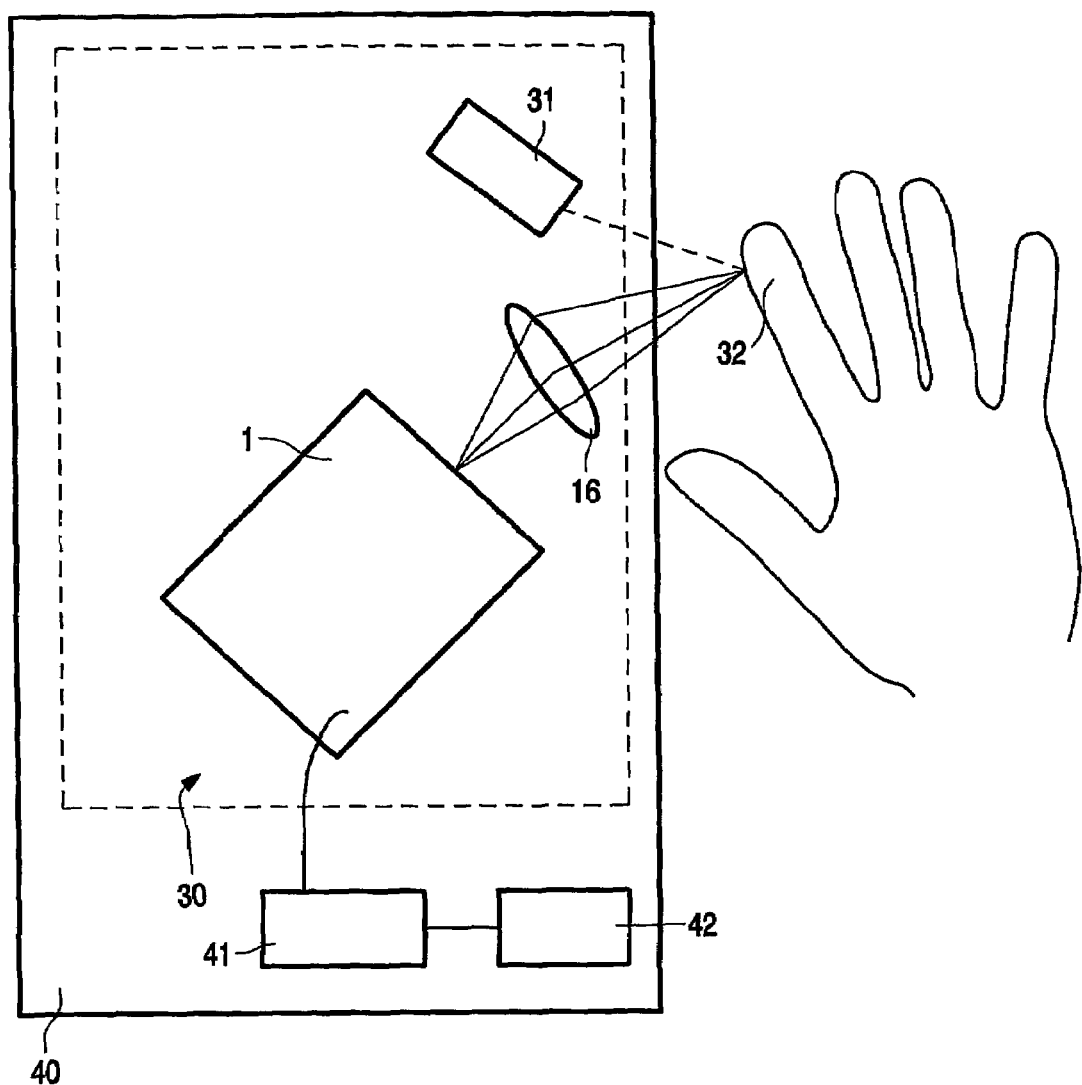
FIG. 6 is a schematic diagram of a blood analysis system comprising a spectroscopic analysis system having an optical analysis system.

The blood analysis system 40 shown in FIG. 6 comprises a spectroscopic analysis system 30. The spectroscopic analysis system 30 comprises a light source 31 for illuminating a sample 32. The light source 31 may be, e.g., a light-emitting diode, a lamp or a laser. In this embodiment the sample 32 is a blood vessel in a finger of a hand. The blood vessel is illuminated by a diode to generate an optical signal having a principal component with an amplitude. This optical signal may be, e.g., a Raman signal having distinct components indicative of distinct blood compounds such as, e.g., glucose, lactate, cholesterol, oxy-hemoglobin and/or desoxy-hemoglobin. Each of the compounds has a corresponding principal component. To analyze the concentrations of these compounds, the spectroscopic analysis system 30 comprises an optical analysis system 1 for determining the amplitude of the principal component of the optical signal as described above.

To determine the concentrations of the compounds, the signals generated by the first detector 5 and the second detector 6 are further processed by a signal processor 41 of the blood analysis system 40. The signal processor 41 has a memory comprising amplitudes of the principal components and the corresponding concentrations of the compounds. The concentrations derived from the amplitudes of the principal component are displayed by a display element 42.

In summary, the optical analysis system 1 is arranged to determine an amplitude of a principal component of an optical signal. The optical analysis system 1 comprises a first detector 5 for detecting the optical signal weighted by a first spectral weighting function, and a second detector 6 for detecting the optical signal weighted by a second spectral weighting function. For an improved signal-to-noise ratio, the optical analysis system 1 further comprises a dispersive element 2 for spectrally dispersing the optical signal, and a distribution element 4 for receiving the spectrally dispersed optical signal and for distributing a first part of the optical signal weighted by the first spectral weighting function to the first detector 5 and a second part of the optical signal weighted by the second spectral weighting function to the second detector 6. The spectroscopic analysis system 30 and the blood analysis system 40 each comprise an optical analysis system 1 according to the invention.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of other elements or steps than those listed in a claim. The word "a" or "an" preceding an element does not exclude the presence of a plurality of such elements.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An optical analysis system for determining an amplitude of a principal component of an optical signal, the optical analysis system comprising:
    a first detector for detecting the optical signal weighted by a first spectral weighting function,
    a second detector for detecting the optical signal weighted by a second spectral weighting function,
    a dispersive element for spectrally dispersing the optical signal, and
    a distribution element for receiving the spectrally dispersed optical signal and for distributing a first part of the optical signal, weighted by the first spectral weighting function, to the first detector and a second part of the optical signal, weighted by the second spectral weighting function, to the second detector.

2. An optical analysis system as claimed in claim 1, wherein the principal component comprises a positive part in a first spectral range and a negative part in a second spectral range, the first part of the optical signal weighted by the first spectral weighting function corresponding to the positive part, the second part of the optical signal weighted by the second spectral weighting function corresponding to the negative part, the first detector and the second detector being coupled to a signal processor arranged to subtract a signal generated by the second detector from a signal generated by the first detector.

3. An optical analysis system as claimed in claim 1, wherein the principal component comprises a first principal component and a second principal component, the first part of the optical signal weighted by the first spectral weighting function corresponding to the first principal component, the second part of the optical signal weighted by the second spectral weighting function corresponding to the second principal component.

4. An optical analysis system as claimed in claim 1, wherein the distribution element has a surface for receiving the spectrally dispersed optical signal, the surface comprising a first set of surface elements and a second set of surface elements, the surface elements of the first set being arranged to distribute the spectrally dispersed optical signal to the first detector, the surface elements of the second set being arranged to distribute the spectrally dispersed optical signal to the second detector.

5. An optical analysis system as claimed in claim 1, wherein the distribution element comprises an array of liquid crystal elements arranged to form a first set of sub-arrays having refractive index gradients, and a second set of sub-arrays having refractive index gradients, the sub-arrays of the first set being arranged to distribute the spectrally dispersed optical signal to the first detector, the sub-arrays of the second set being arranged to distribute the spectrally dispersed optical signal to the second detector.

6. An optical analysis system as claimed in claim 1, wherein the dispersive element is arranged to disperse the optical signal in a dispersive plane and the optical analysis system further comprises a focusing member for focusing the dispersed optical signal, the focusing member having a first focal distance in the dispersive plane and a second focal distance in a plane perpendicular to the dispersive plane, the first focal distance being different from the second focal distance.

7. An optical analysis system as claimed in claim 6, further comprising a further focusing member for focusing the first part of the optical signal on the first detector.

8. An optical analysis system as claimed in claim 7, further comprising a further dispersive element for spectrally recombining the first part of the optical signal prior to focusing the first part on the first detector.

9. A spectroscopic analysis system comprising:
   a light source for illuminating a sample, thereby generating an optical signal having a principal component with an amplitude, and
   an optical analysis system for determining the amplitude of the principal component of the optical signal as claimed in claim 1.

10. A blood analysis system comprising a spectroscopic analysis system as claimed in claim 9.

* * * * *